US005331010A

United States Patent [19]

Newman et al.

[11] Patent Number: 5,331,010
[45] Date of Patent: Jul. 19, 1994

[54] 1-PHENYLA IKANECARBOXYLIC ACID DERIVATIVES AS ANTICONVULSANT AND NEUROPROTECTIVE AGENTS

[75] Inventors: Amy H. Newman; Silvia N. Calderon, both of Silver Spring; Frank C. Tortella, Columbia, all of Md.

[73] Assignee: The United States of America as represented by the Secretary of the Army, Washington, D.C.

[21] Appl. No.: 715,082

[22] Filed: Jun. 5, 1991

[51] Int. Cl.5 .................... A01N 37/18; A01N 33/02; C07C 233/00
[52] U.S. Cl. .................................. 514/617; 514/659; 564/180; 564/306
[58] Field of Search ................ 564/180, 306; 560/102; 514/617, 659

[56] References Cited

U.S. PATENT DOCUMENTS 2,842,585  7/1958  Morren et al. ...................... 560/102

Primary Examiner—José G. Dees
Assistant Examiner—Joseph M. Conrad
Attorney, Agent, or Firm—Werten F. W. Bellamy; John Francis Moran

[57] ABSTRACT

The compounds belong to the class of non-narcotic, non-opiate derivatives of the 1-phenylalkanecarboxylic acid basic structure useful as anticonvulsant and neuroprotective agents. The compounds include novel derivatives as well as previously published species. Methods for controlling convulsions in a variety of pharmaceutical formulations and modalities are also provided.

17 Claims, 1 Drawing Sheet

1-PHENYLAlKANECARBOXYLIC ACID DERIVATIVES AS ANTICONVULSANT AND NEUROPROTECTIVE AGENTS

FIELD OF THE INVENTION

This invention pertains to a group of compounds which exhibit surprising anticonvulsant and neuroprotective properties, and methods for their use in controlling seizures or convulsions. The compounds are 1-phenylalkanecarboxylic acid derivatives. The invention is also directed to pharmacological methods of their use as effective anticonvulsant and neuroprotective agents.

BACKGROUND OF THE INVENTION

One of the challenges of the science of neurological pharmacology is the control of different types of convulsions (as characterized by the clinical manifestations of the attacks and by specific patterns in the electroencephalogram (EEG)) with pharmaceutical agents. The challenge is heightened by the fact that many anticonvulsant compositions known to the art of pharmacy introduce toxic side effects to patients being administered treatments containing them. A noteworthy example is the impairment of the clinical efficacy of valproic acid for treating symptoms of childhood and adolescent epilepsy by potential embryotoxicity and hepatotoxicity. Pharmaceutical compounds which potentiate (i.e. enhance the potency of) anticonvulsant drugs have been developed and introduced into the field to help meet this heightened challenge. Relatively few compounds are known which have stand-alone convulsion control properties. There is a need for compounds having inherent ability to control seizures or convulsions as well as concurrent properties of potentiating other anticonvulsant drugs without introducing toxic side effects to patients requiring this treatment. It is also highly desirable for an anticonvulsant or neuroprotective agent to be effective against a wide a range of convulsion types. Drugs with different treatment and potentiating profiles enable pharmaceutical and medical practitioners to reach a wider range of patients requiring treatment with greater flexibility and lower risk of harm or discomfort through unavoidable side effects. The present invention in its various aspects helps meet the needs of this challenging field.

Carbetapentane [1-phenylcyclopentanecarboxylic acid 2-(2-diethylaminoethoxy)ethyl ester] has the following structural formula:

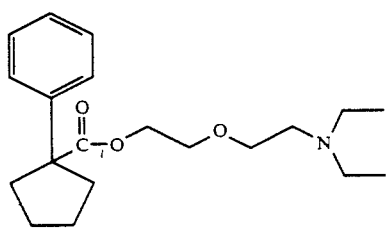

This compound belongs to a class of compounds that may be characterized as non-narcotic, non-opiate antitussives, which is a fairly broad class of compounds that are believed to bind to specific sites in the central nervous system (U.S. Pat. No. 4,694,010). Many compounds which fall within this class are available from commercial sources or may be synthesized using well known techniques. The cough suppressant property of carbetapentane, or antitussive compositions containing it, has been disclosed in U.S. Pat. Nos. 4,694,010; 4,898,860; 4,892,877; and 4,906,638.

It has been shown that some non-narcotic, nonopiate antitussives enhance the potency of some anticonvulsant drugs. This effect, often called "potentiation" is manifested by the lowering of the median effective dose ($ED_{50}$) of anticonvulsant drugs which are coadministered with a potency enhancing agent. Initial studies in this particular field were conducted to test the diphenylhydantoin potentiating properties of dextromethorphan (D-3-methoxy-N-methylmorphinan), a member of the class of unnatural, non-narcotic opioid enantiomers [(+)-morphinans], see U.S. Pat. No. 4,694,010; Mol. Pharmacol. 23:619-628 and 23:629-640 (1983); and Brain Res. 383:314 (1986). The practical effect of the discovery that non-narcotic compounds such as carbetapentane, caramiphen, dextromethorphan and others would enhance the potency of powerful anticonvulsant agents was that the maintenance dosages of the anticonvulsant agents, which characteristically have toxic side effects, could be reduced and rendered safer. Carbetapentane potentiates some anti-convulsant compounds, such as diphenylhydantoin (phenytoin), and other antiepileptic hydantoins. In addition, carbetapentane has some anticonvulsant activity independent of its potentiating properties. Some compounds which can be derived from the basic phenylalkanecarboxylic acid structure have been suggested as potential spasmolytic agents (British Patent No. 753,779). The present invention provides compounds with surprising anticonvulsant and nuroprotective properties, and pharmacological methods for using them without dependence, behavioral modification, toxicity, undesirable side effects, or other liabilities that characterize many prior art compounds and treatment modalities.

SUMMARY OF THE INVENTION

It has been discovered that some novel compounds as well as a previously published species derived from the phenylalkane carboxylic acid basic structure have inherent anticonvulsant or neuroprotective properties. Compounds possessing these properties are provided in this invention. Accordingly, this invention is directed primarily to a group of compounds which have anticonvulsant and/or neuroprotective activity. The invention is also directed to methods for treating convulsive disorders using compounds of the invention in a variety of pharmaceutical preparations and modalities.

DETAILED DESCRIPTION OF THE INVENTION

Figure 1:
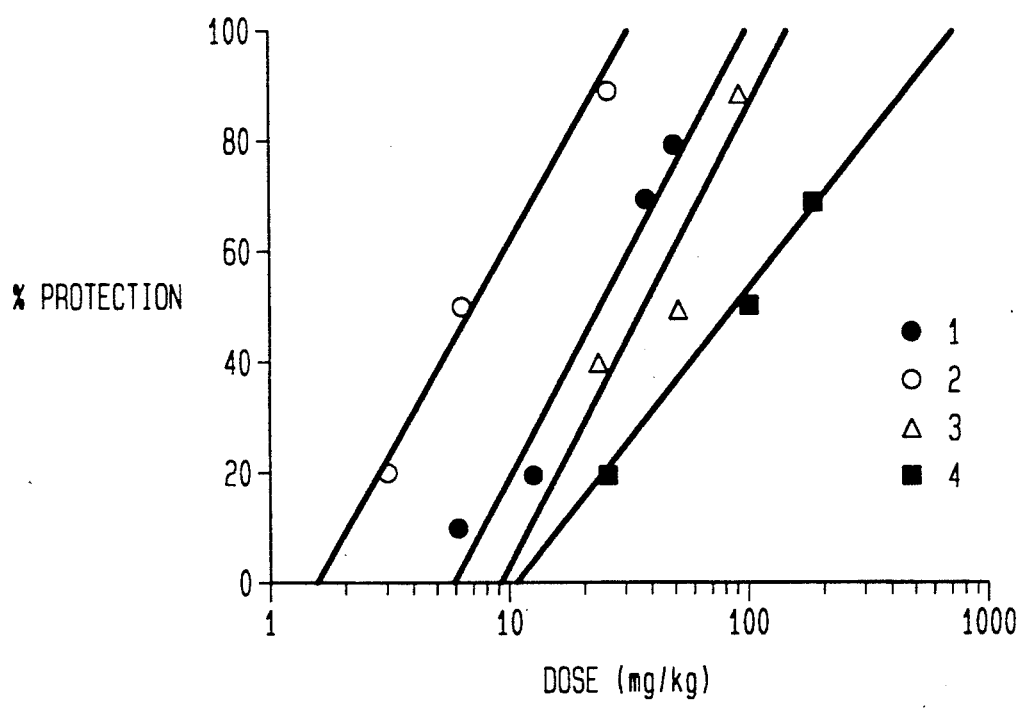
FIG. 1 is a semilog plot of the doses at which a given anticonvulsant compound controls convulsions in a corresponding percentage of the subject animals tested.

The present inventors have prepared a group of compounds including some novel species and have discovered that the compounds surprisingly have potent anticonvulsant and neuroprotective properties. A method for treating convulsions and other neurological disorders exhibiting the same or a closely similar biochemical pathway of symptomatology using compounds of the invention has been developed in accordance with these discoveries.

The compounds of this invention are 1-phenylalkanecarboxylic acid derivatives which have anticonvulsant and/or neuroprotective properties as established by testing with laboratory animals. Preferred compounds of the invention are more potent than prior art compounds as showed by standard laboratory testing described further below, and provide therapeutic treatment without the undesired side effects that characterize some compounds of the prior art. The invention is also directed to methods of using the compounds in a variety of acceptable pharmaceutical formulations.

The compounds of the present invention have the following formula:

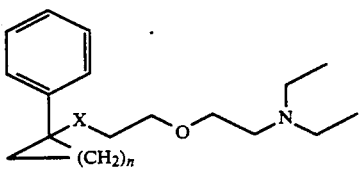

in which X is $-C(=O)O-$, $-CH_2-O-$, $-C(=O)NH$, $-CH_2NH$, or $-CH_2N(C_2H_5)$; and n is an integer 1 through 5, inclusive, provided that when X is $-C(=O)O-$, then n may not be 3.

An anticonvulsant or neuroprotective compound of this invention may be administered alone or as part of a pharmaceutical formulation, and in either case administration may be by any suitable route including oral, rectal, nasal, topical (including buccal and sublingual), and parenteral (including subcutaneous, intramuscular, intravenous and intradermal) with oral or parenteral being preferred. It will be appreciated that the preferred route may vary with, for example, the condition and age of the recipient or the type, nature, and severity of the convulsion. A preferred dose is in the range of 1 to 1,000 mg of a compound of the invention as active ingredient, alone or in a pharmaceutical formulation.

It is preferable to present the active anticonvulsant and neuroprotective compounds of this invention as part of a pharmaceutical formulation. The formulations of this invention comprise at least one administered ingredient as defined above, together with one or more acceptable carriers, flavorings or coatings where suitable, and optionally other therapeutic agents. The carrier(s) must be acceptable in the sense that they must be compatible with the other ingredients of the formulation and they must not be harmful to the recipient.

The formulations may conveniently be presented in unit dosage form and may be prepared by any methods practiced in the art of pharmacy. In general, formulations are prepared by bringing the active ingredients into association with finely divided solid carriers, liquid carriers, or both, and then, if necessary or desired, shaping the product. Formulations useful in the practice of the present invention which are suitable for oral administration may be presented as discrete units such as capsules, cachets, or tablets containing a predetermined amount of the active ingredient; as a powder or granules; or as a solution or suspension in an aqueous or non-aqueous liquid. Preferred unit-dosage forms are liquid formulations for injection or oral administration, and tablets, lozenges, capsules or cachets, also suitable for oral administration.

Compressed tablets may be prepared by compressing with suitable means the active ingredients in a free-flowing form such as a powder or granules, optionally mixed with a binder, lubricant, diluent, preservative, surface-active or dispersing agent. Molded tablets may be prepared with suitable molding means such as punching or compressing the active ingredient and any binders or fillers in a tabletting machine. A mixture of the powdered compound moistened with an inert liquid diluent may also be used. Tablets may be optionally coated or scored and may be formulated so as to provide slow or controlled release of the active ingredient contained in the tablet. Tablets may optionally contain other ingredients, such as additional therapeutic agents. Soft shell gelatin capsules used as pharmaceutical coatings are suitable for orally administered formulations of this invention, also.

Formulations suitable for topical administration include lozenges comprising the ingredients in a flavored medium, pastilles comprising the active ingredient in an inert medium such as gelatin or glycerin. A preferred topical delivery system is a transdermal patch containing the ingredient to be administered.

A suitable formulation for nasal administration may include a carrier comprising a solid, coarse powder having particulate size averaging 20 to 500 microns in diameter. Such a formulation would be administered by rapid inhalation through the nasal passage, for example, from a container of the powder held close to the nose. Suitable formulations including a liquid carrier might include aqueous or oily solutions of the active ingredient. A preferred system of delivery for nasal administration is a nasal spray.

Suitable formulations for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents and thickening agents. The formulations may be presented in unit-dose or multi-dose containers, for example sealed ampules and vials including those suitable for disposal after use, and may be stored in a freeze-dried (lyophilized) condition requiring only the addition of the sterile liquid carrier, such as water for injections, immediately prior to use. Extemporaneous injection solutions and suspensions may be prepared from sterile powders, granules and tablets of the kind previously described.

Preferred unit-dose formulations are those that contain a daily dose or unit, daily sub-dose or appropriate fractional dose or sub-dose, of the administered ingredient. Formulations comprising the compounds of this invention may include other agents conventional in the art pertaining to the type of formulation in question. For example, formulations suitable for oral administration may include flavoring agents, or coatings to facilitate swallowing or to mask an unpleasant taste if a flavoring is not used or is not completely effective. This invention covers the compounds listed above which are 1-phenylalkanecarboxylic acid derivatives showing useful and effective anticonvulsant or neuroprotective activity in mammals in the form of their free bases or appropriate salts, such as hydrochlorides, oxalates, tartrates, fumarates, etc., by standard pharmacological testing.

Effective methods of synthesizing novel compounds of the invention will be described in relation to the reaction schemes and synthetic examples set forth below.

SYNTHESIS

For brevity in the following discussion, chemical compounds which appear herein will be identified by reference numerals which will apply consistently to their respective corresponding species throughout the reaction scheme diagrams, examples, etc. that follow. The numerals correspond to compounds as indicated in the following table, using the basic reference structure defined above. Other compounds of the invention for which synthesis is not specifically described in a working example may be prepared by following the techniques described in the literature cited herein and the techniques of the examples, using the examples and the reaction schemes as guidance. All cited literature is incorporated by reference. Scheme I illustrates the synthetic procedures described in detail in Examples 1 and 2. Scheme II corresponds to the synthetic chemistry of Example 3.

Chemistry

Melting points were determined using a Thomas-Hoover capillary melting point apparatus and are uncorrected. $^1$H NMR spectra were obtained using either a Bruker AC 300 MHz or a Varian XL 300 MHz NMR spectrometer, with trimethylsilane as the internal standard with both apparatuses. IR spectra were determined with a Nicolet Model 105 IR spectrometer using either potassium bromide pellets or chloroform cells. EIMS and CIMS (chemical inonization-NH$_3$) were obtained on a Finnegan 1015 mass spectrometer. Flash column chromatography (silica gel, grade 60, 230–400 mesh, Aldrich Chemical Company, Milwaukee, Wis.) was used for purification. Product purity was tested by thin layer chromatography (silica gel GF, Analtech, DE); the solvent system used was CHCl$_3$:CH$_3$OH:N-H$_4$OH (90:10:1) unless otherwise noted. Elemental analyses were performed by Spang Micro Analytical Laboratory, Eagle Harbor, Mich. All new compounds exhibited satisfactory mircroanalyses for C, H, and N within 0.4% of theoretical values and/or mass, NMR and IR spectral data consistent with the structures assigned.

TABLE 1

| Reference Numeral | n | X |
|---|---|---|
| 1 | 3 | —CO$_2$— |
| 2 | 3 | —CH$_2$—O— |
| 3 | 4 | —CH$_2$—O— |
| 4 | 4 | —CO$_2$— |

EXAMPLE 1

0-[2-(2-Diethylaminoethoxy)-ethyl]-1-phenyl-1-cyclopentanemethanol (2)

Step A

Methyl-1-phenyl-1-cyclopentanecarboxylate

A solution of 1-phenyl-1-cyclopentanecarboxylic acid (2.00 g, 10.51 mmol) in 30 mL methanol saturated with HCl was stirred at reflux for two hours. The reaction mixture was allowed to cool and the solvent was evaporated. The residue was dissolved in 50 mL dichloromethane and washed with 2N sodium hydroxide (3×25 mL). The organic layer was washed with water (2×25 mL) and dried (Na$_2$SO$_4$). Evaporation of the solvent gave 1.89 g (88%) of methyl-1-phenyl-1-cyclopentanecarboxylate as a pale yellow liquid and was used in the next step without further purification. CIMS 205 m/z (M+1).

Step B

1-Phenylcyclopentanemethanol

A solution of the product of Step A (3.00 g, 14.71 mmol) in 10 mL THF was added dropwise to a suspension of LiAlH$_4$ (1.25 g, 33.09 mmol) in 25 mL dry THF. The reaction mixture was stirred at reflux for three hours. The excess LiAlH$_4$ was destroyed following the method described in *Reagents for Organic Synthesis*, Vol 1 [1967] p. 584 (J. Wiley & Son), by quenching the cooled reaction mixture with the addition of 1.25 mL water, followed by the addition of 1.25 mL 154 sodium hydroxide (w/v), followed by the addition of 3.75 mL water. The resulting aluminum salts were separated by filtration and washed with water (5×1 mL). The product was extracted with ether (3×25 mL) and dried (Na$_2$SO$_4$). Evaporation of the solvent gave 2.07 g (88%) of 1-phenylcyclopentanemethanol as a white solid, mp 41°–44° C. (the literature value of mp, *J. Org. Chem.* 27:3434 (1962), is 43°–44° C.).

Step C 2-(2-Diethylaminoethoxy)-ethyl Chloride

A modification of the procedure described in *J. Am. Chem. Soc.* 76:3163 (1954) was used to obtain this compound, beginning with the dropwise addition of thionyl chloride (17.02 mL, 233.42 mmol) to a solution of 2-(2-di-ethylaminoethoxy)-ethanol in benzene (100 mL). The reaction mixture was stirred at reflux for 1.5 hours and the volatiles were removed under diminished pressure. The oily residue crystallized in ether, was nearly homogeneous by TLC, and was used without further purification. The HCl salt obtained in this reaction was very hygroscopic. Attempts at purification of the free base via distillation resulted in decomposition. CIMS 180 m/z (M+1), 183 m/z (M+3).

Step D

0-[2-(2-Diethylaminoethoxy)-ethyl]-1-phenyl-1-cyclopentanemethanol (2)

A solution of the product of Step B (2.21 g, 12.56 mmol) in dry DMF (10 mL) was carefully added to NaOH (1.00 g, 25.12 mmol, 60% suspension in mineral oil) previously washed with petroleum ether (4×5 mL), under an atmosphere of argon, at 0° C. After the addition was complete the reaction mixture was stirred at room temperature for 30 minutes. The HCl salt of Step C (13.56 g, 62.78 mmol) was dissolved in 10% sodium hydroxide (50 mL) and the free base was extracted with chloroform (5×25 mL), dried (Na$_2$SO$_4$) and the solvent was evaporated under diminished pressure. The dark orange residue was added dropwise to the reaction mixture. The addition funnel was washed with DMF (5 mL) and the reaction mixture was stirred overnight at 95°–100° C. The resulting mixture was carefully quenched with water (5 mL) and the product was extracted with ether (2×25 mL). The organic layer was washed with 1N HCl (3×25 mL). The ether layer was dried (Na$_2$SO$_4$) and evaporated, affording unreacted product of Step B starting material (1.40 g, 7.95 mmol). The combined aqueous solution was washed with ether (2×25 mL) basified to pH 9 with NH$_4$OH, extracted with chloroform (3×25 mL) and dried (Na$_2$SO$_4$). Removal of the solvent in vacuo afforded Compound 2 as a pale yellow oil (0.74 g, 50% yield based on recovered starting material). The oxalate hemihydrate salt was obtained by dissolving the free base (0.74 g, 2.31 mmol) in a minimal volume of methanol and adding it to a solution of oxalic acid (0.21 g, 2.31 mmol) in hot methanol. The solvent was evaporated and the salt recrystalized from isopropanol/ether, mp 67°–69° C. $^1$H NMR (D$_2$O) delta 1.22 (t, J=7.3 Hz, 6H), 1.68–1.72 (m, 4H), 1.88–1.90 (m, 4H), 3.10–3.21 (m, 6H), 3.52–3.61 (m, 6H), 3.66 (s, 2H), 7.27–7.46 (m, 5H); CIMS 319 m/z (M+1). Anal. (C$_{22}$H$_{35}$NO$_6$.½H$_2$O) C, H, N.

EXAMPLE 2

0-[2-(2-Diethylaminoethoxy)-ethyl]-1-phenyl-1-cyclohexanemethanol (3)

Step A

1-Phenyl-1-cyclohexanecarboxylic Acid

A modification of the procedure for hydrolyzing nitriles described in *Can. J. Chem.* 40:1909 (1962) was used to obtain this compound. A solution of 1-phenyl-1-cyclohexanecarbonitrile (20.0 g, 108 mmol) in 80 mL 48% HBr was stirred at reflux for four days. The solution was basified with 10% sodium hydroxide (w/v) to pH 8-9, then washed with ether (3×25 mL). The aqueous layer was acidified with 1N HCl to pH of 2-3, then the product was extracted with ether (4×25 mL), giving 15.9 g of 1-phenyl-1-cyclohexanecarboxylic acid (72%), mp 118°–121° C. (compared with the literature value, *J. Am. Chem. Soc.* 56:715 (1934), of 121° C.).

Step B

Methyl-1-phenyl-1-cyclohexanecarboxylate

This compound was prepared (1.91 g, 8.76 mmol, 89%) from the product of Step A (2.00 g, 9.8 mmol) following the procedure for synthesis of methyl-1-cyclopentanecarboxylate as set forth in Step A, Example 1. The product of this step was homogeneous by TLC (ether:C$_2$Cl$_2$, 2:1) and used in the next step without further purification. CIMS 219 m/z (M+1).

Step C

1-Phenylcyclohexanemethanol

This compound was prepared (1.02 g, 5.43 mmol, 62%) from the product of Step B (1.91 g, 8.76 mmol) using LiAlH$_4$ (0.75 g, 37.95 mmol) according to the procedure for synthesizing 1-phenylcyclopentanemethanol set forth in Step B, Example 1, with the exception that this compound precipitated out of solution following the steps of: (a) destroying the excess hydride; (b) separating the aluminum salts by filtration; and (c) washing with water (3×4 mL in this Example). Filtration of the precipitate gave 1-phenylcyclohexanemethanol as a white solid, mp 63°–64° C. (compared with reported value, *J. Org. Chem.* 27:3434 (1962), of 63°–64° C.).

Step D

0-[2-(2-Diethylaminoethoxy)-ethyl]-1-phenyl-1-cyclohexanemethanol (3)

Compound 3 was prepared (1.0 g, 3.0 mmol, 39%) from the product of Step C (1.45 g, 7.63 mmol) according to the procedure for synthesizing compound 2 set forth in Step D, Example 1. The product 3 was purified by flash column chromatography (CHCl$_3$:CH$_3$OH:NH$_4$OH, 90:10:1). The oxalate salt was obtained by dissolving the free base (0.34 g, 1.01 mmol) in a minimal volume of hot methanol and adding it to a solution of 0.09 g oxalic acid (8.75 mmol) in hot methanol. The solvent was evaporated and the salt recrystallized from isopropanol/ether, mp 84°–85° C. $^1$H NMR (D$_2$O) delta 1.24 (t, J=7.3 Hz, 6H), 1.32–1.66 (m, 8H), 2.08–2.13 (m, 2H), 3.12–3.23 (m, 6H), 3.45–3.62 (m, 8H), 7.29–7.53 (m, 5H); CIMS 334 m/z (M+1). Anal. (C$_{23}$H$_{37}$NO$_6$) C, H, N.

EXAMPLE 3

2-(2-Diethylaminoethoxy)-ethyl-1-phenyl-1-cyclohexane carboxylate (4)

A solution of 1-phenyl-1-cyclohexanecarboxylic acid (1.02 g, 5 mmol) and 2.5 mL thionyl chloride in 25 mL toluene was stirred at reflux for two hours under an atmosphere of argon. The solvent was evaporated under diminished pressure and the acid chloride (1-phenyl-1-cyclohexanecarboxyl chloride) was dissolved in 20 mL toluene. A solution of diethylaminoethoxy ethanol (0.85 mL, 5 mmol) and triethylamine (0.75 mL) was added dropwise to the acid chloride solution. The mixture was stirred at reflux for three hours and then was allowed to stand at room temperature overnight. The triethylamine HCl formed in the reaction was separated by filtration and the filtrate was washed with toluene (3×1 mL). The solvent was evaporated and the residue was dissolved in 25 mL 20% NH$_4$OH. The product was extracted with chloroform (3×25 mL) and the combined organic fraction was washed with water (2×25 mL) and dried (Na$_2$SO$_4$). The solvent was evaporated, affording compound 4 as a pale yellow oil (1.72 g, 99%). The citrate salt was prepared by dissolving the free base (0.50 g, 1.44 mmol) in a minimal volume of hot methanol and adding it to a solution of 0.28 g citric acid (1.44 mmol) in hot methanol. Addition of anhydrous ether resulted in the crystalline fumarate salt, which was recrystallized from methanol/ether, mp 86°–87° C. $^1$H NMR (D$_2$O) delta 1.20 (t, J=7.2 Hz, 6H), 1.41–1.85 (m, 8H), 2.38–2.41 (m, 2H), 3.07–3.14 (m, 6H), 3.57–3.70 (m, 4H), 4.28 (t, J=4 Hz, 2H), 7.33–7.50 (m, 5H); CIMS 348 m/z (M+1). Anal. (C$_{27}$H$_{41}$NO$_{10}$) C, H, N.

The utility of the compounds of this invention, described above, for controlling seizures and convulsions has been established through standard laboratory testing. The testing protocol and the results obtained will be described in the following section.

UTILITY

The anticonvulsant activity of the present compounds was assessed by the method of inducing maximal electroshock seizures (MES) in rats using the standard testing protocol conditions hereinafter described:

Animals. Male Sprague-Dawley rates weighing 225-275 g obtained from Zivic Miller Laboratories, Alison Park, Pa., were used for all experiments. Upon delivery the animals were kept in individual pens housed in a temperature controlled laboratory. A standard 12-hour light-dark cycle was maintained. The animals were given food and water ad libitum. The animals were randomly assigned as control group animals or drug-treated animals.

Maximal electroshock seizures (MES) assay. Supramaximal (tonic handlimb extension) seizures were induced in test rates by means of an electric shock apparatus. A current of 60 Hz and 50 mA was delivered transauricularly through miniature alligator clips attached to the pinna of each ear for 2.0 seconds. The shock parameters used in the studies have been shown to induce MES, and not threshold seizures. In general, MES causes a generalized convulsion characterized by an initial tonic forelimb extension (TFE) progressing immediately to tonic hindlimb extension (THE) followed by clonic jerking. The presence or absence of THE was recorded for each MES convulsion.

Experimental protocol. Two groups of animals with n=10 for each group were tested under the conditions described above. Compounds were administered to each test animal by a single subcutaneous injection. There were no signs of overt sedation, ataxia or motor impairment at any time during the MES assay after drug injection.

Drug-treated animals received a single subcutaneous injection of compounds 2, 3 and 4 of this invention in varying doses, as specified below. Carbetapentane (compound 1) was administered in doses ranging from 6.25–50.0 mg/kg. Drug-treated animals were also tested for reaction to diphenyhydantoin (DPH). Active ingredients were diluted in deionized water. In all cases, control animals received respective vehicle treatments (1 mL/kg, sc). All the animals tested, whether in the drug-treated or control groups, were naive to drug and seizure, and each animal was used only once. The dose-response experiments were done at the interval of 30 minutes after injection, the reported time of peak anticonvulsant response for carbetapentane. FIG. 1 plots the anticonvulsant activity of compounds of the invention is comparison with carbetapentane. The utility data in FIG. 1 is presented in a semilog plot of the percentage of seizure protection versus the indicated dosages of the given anticonvulsant compounds. In the figure, the reference numeral 1 signifies carbetapentane; 2 signifies 0-[2-(2-diethylaminoethoxy) ethyl]-1phenyl-1-cyclopentanemethanol; 3 represents 0-[2-(2-diethylaminoethoxy)-ethyl]-1-phenyl-1-cyclohexanemethanol; and 4 denotes 2-(2-diethylaminoethoxy)-ethyl-1-phenyl-1-cyclohexane carboxylate.

The anticonvulsant activity of compounds of the invention in comparison with carbetapentane and diphenylhydantoin as determined by the MES assay experimental protocol described above is summarized in Table 2.

TABLE 2

| Compound | Anticonvulsant | |
|---|---|---|
| | ED$_{50}$ (umol/kg) | mg/kg (s.c.) |
| DPH | 30 | 8 |
| 1 | 48 | 25 |
| 2 | 16 | 7 |
| 3 | 86 | 37 |
| 4 | 173 | 93 |

The invention has been described and illustrated with respect to certain specific embodiments. Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

Scheme I

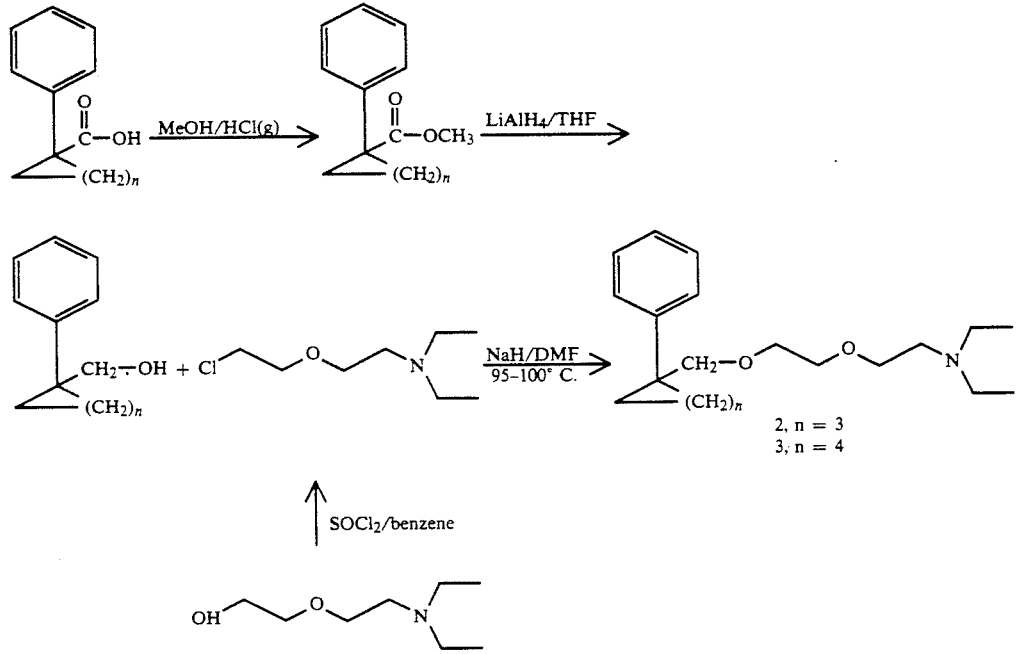

Scheme II

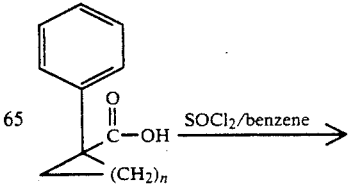

-continued
Scheme II

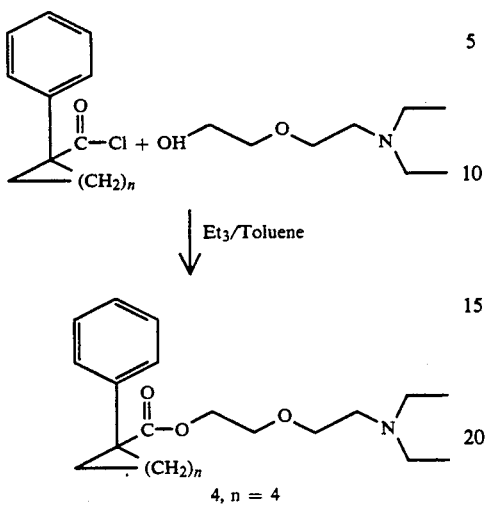

What is claimed is:

1. A compound having the formula:

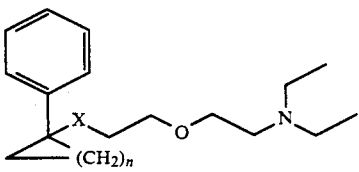

wherein X is —CH$_2$O—, [—C(=O)O—, ] —C(=O)NH, CH$_2$NH, or —CH$_2$N(C$_2$H$_5$), and n is an integer between 1-5; or a pharmaceutically acceptable salt thereof.

2. The compound of claim 1 contained in a liquid injectable dosage form.

3. The compound of claim 1 contained in a liquid oral dosage form.

4. The compound of claim 1 contained in a solid oral dosage form.

5. The compound of claim 1 wherein X is —CH$_2$O— and n is 3, which is 0-[2-(2-diethylaminoethoxy)-ethyl]-1phenyl-1-cyclopentanemethanol.

6. The compound of claim 5 contained in a liquid injectable dosage form.

7. The compound of claim 5 contained in a liquid oral dosage form.

8. The compound of claim 5 contained in a solid oral dosage form.

9. The compound of claim 1 wherein X is —CH$_2$O— and n is 4, which is 0-[2-(2-diethylaminoethoxy)-ethyl]-1phenyl-1-cyclohexanemethanol.

10. The compound of claim 9 contained in a liquid injectable dosage form.

11. The compound of claim 9 contained in a liquid oral dosage form.

12. The compound of claim 9 contained in a solid oral dosage form.

13. A method of treating a mammal for convulsions which comprises administering to said mammal an effective anticonvulsant or neuroprotective amount of a compound having the formula:

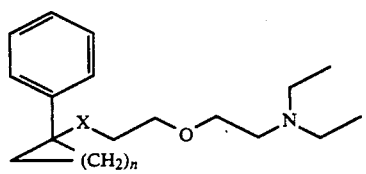

wherein X is —CH$_2$O—, —C(=O)O—, —C(=O)NH, CH$_2$NH, or —CH$_2$N(C$_2$H$_5$), and n is an integer between 1-5, provided that when X is —C(=O)O— then n may not be 3; or a pharmaceutically acceptable salt thereof.

14. The method of claim 13 wherein the anticonvulsant or neuroprotective compound administered is 0-[2-(2-diethylaminoethoxy)-ethyl]-1-phenyl-1-cyclopentanemethanol.

15. The method of claim 13 wherein the anticonvulsant or neuroprotective compound administered is 0-[2-(2-diethylaminoethoxy)-ethyl]-1-phenyl-1-cyclohexanemethanol, 16. The method of claim 13 wherein the anticonvulsant or neuroprotective compound administered is 2-(2-diethylaminoethoxy)-ethyl-1-phenyl-1-cyclohexane carboxylate.

17. The method of claim 13 wherein the amount of the compound to be administered is 1,000 mg or less of active ingredient.

* * * * *